United States Patent [19]

Gray

[11] 4,288,635

[45] Sep. 8, 1981

[54] METHOD FOR THE PREPARATION OF (E)-4-BROMO-2-METHYLBUT-2-EN-1-AL

[75] Inventor: Gary M. Gray, Bethlehem, Pa.

[73] Assignee: J. T. Baker Chemical Co., Phillipsburg, N.J.

[21] Appl. No.: 152,700

[22] Filed: May 23, 1980

[51] Int. Cl.$^3$ ............................................. C07C 47/24
[52] U.S. Cl. ..................................... 568/483; 568/495
[58] Field of Search ................................ 568/483, 495

[56] References Cited

U.S. PATENT DOCUMENTS

| 3,268,430 | 8/1966 | Boris | 568/483 |
|---|---|---|---|
| 3,940,445 | 2/1976 | Werner et al. | 568/483 |
| 4,054,608 | 10/1977 | Re et al. | 568/483 |

FOREIGN PATENT DOCUMENTS 2620968 11/1976 Fed. Rep. of Germany ...... 568/483

OTHER PUBLICATIONS

Fletti–Bianchi et al., "J. Org. Chem." vol. 41 (1976) 1648–1650.

*Primary Examiner*—Werren B. Lone
*Attorney, Agent, or Firm*—George W. Rauchfuss, Jr.

[57] ABSTRACT

A method for the preparation of (E)-4-bromo-2-methylbut-2-en-1-al comprises brominating 3,4-epoxy-3-methyl-1-butene with cupric bromide in the presence of lithium carbonate.

2 Claims, No Drawings

METHOD FOR THE PREPARATION OF (E)-4-BROMO-2-METHYLBUT-2-EN-1-AL

FIELD OF THE INVENTION

This invention relates to a method for the preparation of (E)-4-bromo-2-methylbut-2-en-1-al by brominating isoprene epoxide with cupric bromide in the presence of lithium carbonate.

BACKGROUND OF THE INVENTION

The compound (E)-4-bromo-2-methylbut-2-en-1-al is

DETAILED DESCRIPTION OF THE INVENTION

According to this invention, isoprene epoxide is brominated with a least a stoichiometric proportion of anhydrous cupric bromide, that is, two mols cupric bromide per mol of epoxide. The liquid phase bromination is carried out at a refluxing temperature of from about 80° to about 90° C. and is carried out in any suitable solvent, such as for example, in a chloroform-ethyl acetate mixture.

The reaction is carried out in the presence of lithium